United States Patent [19]

Olivero et al.

[11] Patent Number: 5,326,885
[45] Date of Patent: Jul. 5, 1994

[54] PROCESS OF PREPARING ENRICHED ENANTIOMERS OF GLYCEROL CARBONATE AND DERIVATIVES THEREOF FOR SYNTHESIS OF β-BLOCKERS

[75] Inventors: Alan G. Olivero, Windsor; Jonathan M. Cassel, Healdsburg; James R. Poulsen, Bodega Bay, all of Calif.

[73] Assignee: Cognis, Inc., Santa Ross, Calif.

[21] Appl. No.: 140,799

[22] Filed: Oct. 21, 1993

Related U.S. Application Data

[63] Continuation of Ser. No. 877,556, May 1, 1992, abandoned.

[51] Int. Cl.$^5$ .......................... C07D 317/08
[52] U.S. Cl. .................................. 549/229
[58] Field of Search ........................ 549/229

[56] References Cited

U.S. PATENT DOCUMENTS

| | | | |
|---|---|---|---|
| 2,915,529 | 12/1959 | Bell, Jr. et al. | 260/340.2 |
| 4,732,853 | 3/1988 | Whitesides et al. | 435/123 |
| 4,933,290 | 6/1990 | Cesti et al. | 435/280 |

FOREIGN PATENT DOCUMENTS

| | | | |
|---|---|---|---|
| 328150 | 8/1989 | European Pat. Off. | 549/229 |
| 0388778 | 9/1990 | European Pat. Off. | |
| 406057 | 1/1991 | European Pat. Off. | 549/229 |
| WO87/03584 | 6/1987 | PCT Int'l Appl. | |

OTHER PUBLICATIONS

Scherowsky et al, CA 117-81464p (1992).
Aronsson et al, CA 111-174553h (1988).
Abstract of JP 60 100571, CA 103-141748g (1985).
T. Walle et al., Biochem. Pharmacol., 37, 115-124 (1988).
Hamaguchi et al., J. Agri, Biol. Chem., 49: 1509-1511 (1985).
Chemical Abstract 33428f, vol. 106, No. 5, (1987), p. 589.
Chemical Abstract 155185f, vol. 82, No. 23, (1975), p. 515.
Thomas Walle, et al, "Stereoselective Delivery and Actions of Beta Receptor Antagonists", *Biochemical Pharmacology*, vol. 37, No. 1, 1988, pp. 115-124.

*Primary Examiner*—Cecilia Tsang
*Attorney, Agent, or Firm*—Wayne C. Jaeschke; John E. Drach; Henry E. Millson, Jr.

[57] ABSTRACT

Enriched enantiomers of glycerol Carbonate are produced under the influence of a hydrolytic enzyme, either by selective esterification of racemic glycerol carbonate or by selective hydrolysis of an ester of the racemate. The enriched enantiomeric product is readily converted to starting materials and intermediates useful in the synthesis of enantiomerically pure therapeutic agents, such as β-adrenergic blockers.

5 Claims, No Drawings

PROCESS OF PREPARING ENRICHED ENANTIOMERS OF GLYCEROL CARBONATE AND DERIVATIVES THEREOF FOR SYNTHESIS OF β-BLOCKERS

This application is a continuation of application Ser. No. 07/877,556 filed on May 1, 1992, now abandoned.

BACKGROUND OF THE INVENTION

1. Field of the Invention

The present invention relates to processes for preparing enantiomerically enriched glycerol carbonate and to certain derivatives thereof which are useful as starting materials and intermediates in the synthesis of enantiomerically pure therapeutic agents, particularly β-adrenergic blockers.

2. Statement of Related Art

Many therapeutic compounds are chiral, existing in right-handed (R), and left-handed (S) molecular forms known as enantiomers. Paired enantiomers have different optical activity in that they rotate polarized light in opposite directions; otherwise, they have identical physical properties. The molecular chirality which is characteristic of enantiomers is often due to the presence of an asymmetric carbon, i.e., a carbon atom bonded to four different substituent groups. Generally, the synthesis of compounds possessing an asymmetric center yield a racemate, unless optically active starting materials are used. Although certain therapeutic compounds exist as enantiomers, in many cases they are marketed as a mixture of equal quantities of paired enantiomers, known as a racemate. The therapeutic effect of each member of an enantiomeric pair may differ substantially, however, even though their structures are virtually identical. Recently, concern has arisen that therapeutic agents used in the form of racemates can create health problems, for example, when only one enantiomer is therapeutically effective, whereas the other is inactive, or works to counteract the desired therapeutic effect, or, in some cases, produces undesired side effects. Thus, there is considerable interest among drug manufacturers in making only the enantiomerically pure therapeutic agents.

One such class of therapeutically-active enantiomers is known as the β-adrenergic blockers, or simply β-blockers. These compounds are often used in clinical practice in the form of the racemate, although higher activity is exhibited by the S isomer in comparison with the R isomer. T. Walle et al., Biochem. Pharmacol., 37, 115 (1988).

Over the past decade, the use of hydrolytic enzymes has been proposed to effect resolution of chiral compounds in order to provide enantiomerically pure starting materials for the production of therapeutically-active enantiomers. See, for example, Cesti et al., U.S. Pat. No. 4,933,290 and Whitesides et al., U.S. Pat. No. 4,732,853. In use, however, the enantiomerically enriched starting materials heretofore proposed have certain inherent shortcomings. Glycidol derivatives, for example, are both thermally and chemically unstable. In addition, there are potential health hazards associated with their use.

It would be desirable to develop alternative methods for efficient and effective production of optically active starting materials and/or intermediates which are useful in the preparation of enantiomerically pure therapeutic agents, such as β-adrenergic blockers, and which avoid the above-noted shortcomings of the prior art. Preparation of R and S glycerol carbonate can be accomplished by degradation of sugar derivatives but the method is lengthy and suffers from poor yields.

Insofar as is known, the preparation of an enantiomerically enriched glycerol carbonate via enzymatic methods has not previously been performed successfully. Hamaguchi et al., J. Agric. Biol. Chem., 49:1511 (1985).

SUMMARY OF THE INVENTION

In accordance with the present invention, processes are provided for preparation of enriched enantiomers of glycerol carbonate. One process involves esterifying racemic glycerol carbonate under the influence of a hydrolytic enzyme which selectively esterifies the S isomer of the racemate. Another process involves hydrolyzing the racemate of an ester of glycerol carbonate under the influence of a hydrolytic enzyme which selectively hydrolyzes the ester of the S enantiomer present in the racemate.

The products obtained from the processes of the invention are useful starting materials for the preparation of a substantially enantiomerically pure β-adrenergic blockers, of the formula

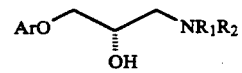

The processes and compounds of the present invention afford manufacturers of enantiomerically pure pharmaceutical products a distinct advantage by avoiding the potential for an inactive enantiomer to interfere with the activity of its therapeutically effective isomer or to produce adverse side effects.

DESCRIPTION OF THE PREFERRED EMBODIMENTS

Racemic glycerol carbonate, which is used as the starting material for preparation of the enriched R enantiomer in accordance with the present invention, is also known by the chemical name 4-hydroxymethyl-1,3-dioxolan-2-one. The racemate is known and may be prepared according to procedures familiar to those skilled in the art. Bell, et. al., U.S. Pat. No. 2,915,529.

The esterification agents used in the practice of this invention may be any saturated or unsaturated carboxylic acid anhydride or carboxylic acid ester, having from 4 to 6 total carbon atoms. Representative of the carboxylic acid anhydrides which may be used in the processes of the invention are acetic, propionic, butyric, valeric, hexanoic, isobutyric and succinic anhydrides. Suitable esters include vinyl esters such as vinyl acetate, vinyl propionate, and vinyl butyrate, as well as other alkyl and haloalkyl esters such as ethyl acetate, methyl propionate, and trichloroethyl acetate. Saturated anhydrides having 4 to 12 carbon atoms are preferred because they have been found to give products of higher enantiomeric purity, with relatively faster reaction times.

The process of preparing an enantiomerically enriched R glycerol carbonate in accordance with the present invention is carried out using a molar ratio of glycerol carbonate to esterifying agent in the range of about 0.1:1 to about 5:1, preferably in the range of 1:0.5 to 1:1 and most preferably in the range of 1:0.6 to 1:0.8.

Various commercially available hydrolytic enzymes may be used in the processes of the invention. Commercially available lipases have produced good results. Microbiologically derived lipases are preferred; however, lipases of animal or plant origin may be used if desired. Particularly satisfactory results have been obtained using a commercial lipase of Pseudomonas cepacia (Amano Ps lipase). Most preferred is a strain of Pseudomonas sp. (ATCC 21808) which is the subject of U.S. Pat. application Ser. No. 07/600,287, filed on Oct. 19, 1990 and which is commonly assigned with the present application.

The amount of enzyme utilized is generally within a weight percentage of 0.001 to 1000% relative to the racemic glycerol carbonate. The weight percentage of enzyme is preferably in the range of 0.01 to 10%, and most preferably 0.1 to 2%, based on the weight of the racemate. The enzyme may be unsupported or, preferably, it may be immobilized on a suitable substrate in order to enhance stability and facilitate recovery and further utilization. Porous substrates having a high surface area are particularly useful, such as diatomaceous earth, alumina, silica, acrylic resins, polystyrene resins and phenol-formaldehyde resins. Immobilization of the enzyme on the selected carrier is readily achieved using techniques well known to those skilled in the art.

Enrichment of the R enantiomer of glycerol carbonate is carried out by forming a reaction mixture of the racemate and the esterifying agent in a suitable reaction medium and adding thereto the hydrolytic enzyme. However, the order of addition of the reactants and enzyme to the reaction mixture is not critical. An organic solvent is the preferred reaction medium. Aqueous reaction systems are less desirable due to the difficulty involved in recovering the desired product from aqueous media. Included among the organic solvents suitable for use in the practice of this invention are ethyl acetate, propyl acetate, butyl acetate, dimethoxyethane, ethyl propionate, and methylene chloride. Carboxylic acid esters are particularly preferred as a reaction medium. If desired, an excess of the esterifying agent may be used as the reaction medium.

The molecular concentration of the racemate in the reaction mixture may range from 0.1 M to 2.0 M and preferably is in the range of about 0.8 M to 1.2 M.

The reaction conditions for conversion of the racemate to the enantiomerically enriched product are not critical. The reaction is typically carried out within a temperature range from about 0° C. to about 80° C., the preferred temperature range being about 20° C. to 40° C. The reaction is most preferably carried out at room temperature (about 25° C.). The reaction time may range anywhere from about 10 minutes to about 72 hours, depending on the nature of the enzyme used, the conversion rate desired and other reaction conditions. The reaction mixture should preferably be vigorously stirred during the course of the reaction. In the case of the preparation of an enantiomerically enriched R-glycerol carbonate, the reaction is typically run to 70-75% conversion to obtain the desired isomer, which is about 92-97% enantiomerically pure. It should be noted that the enriched R enantiomer of glycerol carbonate resulting from the process described above is the unreacted enantiomer. The actual product of the reaction is the ester which is enriched in the S enantiomer, the latter being approximately 40-60% enantiomerically enriched.

The course of the reaction can be monitored by GC (TMS derivative), using a chiral column to determine the extent of conversion and enantiomeric excess. Once the desired conversion is achieved, the enzyme is removed by filtration and glycerol carbonate extracted away from the undesired ester with water. The aqueous solution can be washed with an organic solvent to remove traces of organic soluble by-products. The water is removed under vacuum to provide R-glycerol carbonate in an enantiomerically enriched form.

The reaction can alternatively be run continuously by passing a solution of racemic glycerol carbonate and the anhydride in an organic solvent through a column of the enzyme at an optimum flow rate to achieve the resolution. The product of the continuous flow system is worked-up similar to that described above.

An alternative process for the preparation of enriched S enantiomer of glycerol carbonate involves enzymatic hydrolysis of racemic esters of glycerol carbonate, which may be the enantiomerically enriched esters of glycerol carbonate prepared in the manner described above. In carrying out the latter reaction, the same general reaction conditions are utilized as those described above with respect to the esterification process, except that an alcohol, such as methanol or ethanol, or water is used in place of the esterifying agent and an ester of glycerol carbonate is used in place of racemic glycerol carbonate.

The enantiomerically enriched isomers of glycerol carbonate, prepared as described above, are readily converted to starting materials useful for the synthesis of $\beta$-adrenergic blockers, such as S-atenolol, S-toliprolol, S-bunolol, S-penbutolol, S-propanolol, S-timolol and other aryloxypropanolamine antihypertensive agents [Merck Index, 11th ed. p. THER-5, THER-14]. Such starting materials, having the formula

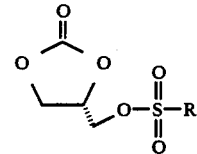

are conveniently prepared by contacting a solution of the enantiomerically enriched glycerol carbonate with the appropriate alkyl or aryl sulfonyl chloride in the presence of a base such as tertiary amines, pyridines, or imidazoles. Specific examples of compounds which may be prepared in this manner include compounds of the formula set forth immediately above wherein R is phenyl, 4-methylphenyl, 4-nitrophenyl, 3-nitrophenyl, and 4-chlorophenyl. It has been experimentally demonstrated that these cyclic carbonate starting materials undergo nucleophilic attack by phenols, amines, and halides, thereby causing ring opening with loss of $CO_2$.

Synthesis of $\beta$-adrenergic blockers using the above-described starting materials may be accomplished according to the following reaction scheme:

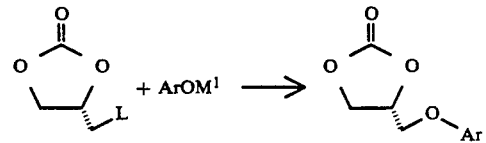

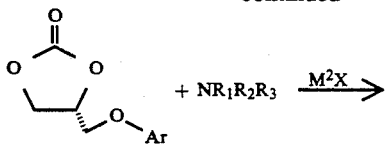

wherein L is a suitable leaving group, such as —$O_3SR$, Cl, Br, I; Ar is a substituted or unsubstituted aryl group having from 6–20 carbon atoms, a substituted furan, thiophene, or indole, having 6–20 carbon atoms, the aryl substitutents being alkyl, aryl, carboxyalkyl, cyano, alkoxy, and aryloxy; and the $R_1$, $R_2$ amine substituents are independently selected from the group consisting of hydrogen, alkyl, aryl, and benzyl with amine substituent $R_3$ being hydrogen; wherein $M^1$ is Li, Na, K; $M^2$ is Li, Na, K, Mg, $N(CH_3)_4$, $N(butyl)_4$, or $P(butyl)_4$ and X is F, Cl, Br, I.

The intermediates prepared from the reaction of enantiomerically enriched glycerol carbonate and alkyl or aryl sulfonyl chlorides in the foregoing reaction scheme are believed to be a novel compositions of matter, and forms a part of the present invention. It is also believed that the alkyl or aryl sulfonyl iodides and bromides are also novel compositions of matter.

The following examples describe the processes and compounds of the present invention in further detail, including the manner and process of making and using the same, and set forth the best mode presently contemplated by the inventors for carrying out the invention. The examples are provided for illustrative purposes only, and are not intended to limit the scope of the invention in any way.

EXAMPLE 1

Glycerol carbonate (5.5 g, 46 mmoles) was dissolved in butyl acetate (55 ml) and the solution placed in a round bottom flask. Decane (550 mg - internal standard) and propionic anhydride (4.5 ml, 35 mmoles) were next added. To the solution was added the biocatalyst (550 mg) which was 20% formulated *Pseudomonas cepacia* lipase (Amano Ps lipase) immobilized on Celite 577. The reaction was stirred at room temperature until the propionic anhydride was consumed. GC analysis on a chiral GC column (TMS derivative) showed that the glycerol carbonate present was 94.5% the R enantiomer and 5.5% the S enantiomer. The lipase was filtered off and the organic solution extracted several times with water. The aqueous solution of glycerol carbonate was washed 3 times with butyl acetate and the water removed under vacuum to obtain 1.35 g of product which was shown again by GC to be glycerol carbonate in R:S ratio of 94.8:5.2.

EXAMPLE 2

Racemic glycerol carbonate (200 mg, 1.69 mmoles) is dissolved in ethyl acetate (2 ml) and decane (20 mg) added as an internal standard. Acetic anhydride (160 ul, 1.69 mmoles) and the biocatalyst (20 mg - 20% loading on Celite 577) are added. The reaction is stirred at room temperature for the length of time indicated in the table below and the enantiomeric excess of the products (TMS derivative) determined by gas chromatography using a chiral column (Cyclodex B - J&W Scientific).

| Reaction | Enzyme | Time | Convers. | Glycerol Carbonate R:S | Ester R:S |
| --- | --- | --- | --- | --- | --- |
| 2.A | Ps. ATCC 21808 (COGNIS) | 4 h | 69% | 96:4 | 30:70 |
| 2.B | Ps. cepacia (Amano) | 4 h | 62% | 92:8 | 24:76 |
| 2.C | Porcine Pancreatic (Sigma) | 96 h | 29% | 53:47 | 48:52 |
| 2.D | Candida cylidracea (Aldrich) | 48 h | 15% | 52:48 | 50:50 |
| 2.E | Humicola languinosa | 24 h | 29% | 55:45 | 32:68 |

EXAMPLE 3

Racemic glycerol carbonate (20.0 g, 169 mmole) was dissolved in propyl acetate (200 ml) and decane (2.0 g) added as an internal standard. Hexanoic anhydride (27.0 g, 126 mmoles) was added and the biocatalyst (4.0 g - Amano Ps/30 on Celite 577) added. The reaction was stirred at room temperature for 3 hours and GC (Cyclodex-B column) showed glycerol carbonate present to be in a R:S ratio of 88:11. The biocatalyst solution was filtered and the solvent replaced with a 1:1 hexane:propyl acetate. The organic layer was extracted several times with water and the aqueous layer washed twice with propyl acetate. The water was removed under vacuum to produce 5.2 grams of the enantiomerically enriched R-glycerol carbonate.

EXAMPLE 4

Sulfonates of R-glycerol carbonate were prepared as follows:

A. Tosylate of R-Glycerol Carbonate (4-[[[(4-methylphenyl)sulfonyl]oxy]methyl]-1,3-dioxolan-2-one).

In a 50 ml round bottom flask was placed p-toluenesulfonylchloride (2.28 g, 12 mmoles) and dry THF (5 ml). Triethylamine (2.1 ml, 15 mmoles) was added and the reaction stirred at 0° C. To this solution was added dropwise a solution of glycerol carbonate (1.18 g, 10 mmoles) in 5 ml THF. The reaction was stirred for 16 hours and allowed to come to room temperature. The solution was diluted with 50 ml ethyl acetate and the solution washed with water (3×50 ml), 0.2M HCl (1×10 ml), and saturated sodium bicarbonate (1×10 ml). The organic layer was dried over anhydrous magnesium sulfate, filtered and the solvent removed under vacuum to yield 2.5 g of crude product. The material was recrystallized two times from hexane:ethyl acetate to yield white crystals shown by NMR to be the desired tosylate. [α]=+1.67 (c=1, dioxane). 1HNMR ($CD_3CN$): 7.79 (d, 2H, 7.44 (d, 2H), 4.90 (m, 1H), 4.48 (t, 1H), 4.2 (m, 3H), 2.44 (s, 3H). C13NMR ($CD_3CN$): 155.54, 146.94, 132.96, 131.16, 128.85, 74.60, 69.89, 66.51.

B. 3-Nitrobenzenesulfonate of R-Glycerol Carbonate (S-4-[[[(3-nitrophenyl)sulfonyl]oxy]methyl]-1,3-dioxolan-2-one).

The procedure of Example 2A was followed, except 3-nitrobenzenesulfonylchloride (2.65 g, 12 mmole) was used instead of p-toluenesulfonylchloride to yield 2.57 g of the 3-nitrobenzenesulfonate. The product was recrystallized two times from hexane:ethyl acetate. $[\alpha]_D = +34.99$ (c=1, dioxane). 1HNMR (DMSO): 7.74 (dd, 1H), 7.66 (t, 1H), 7.47 (dd, 1H), 7.11 (t, 1H), 4.12 (m, 1H), 3.60 (m, 3H), 3.27 (dd, J=8.7, 6.0 Hz, 1H). C13NMR (DMSO): 154.19, 148.07, 136.00, 133.65, 132.06, 129.19, 122.73, 73.60, 70.58, 65.35.

C. 4-Nitrobenzenesulfonate of R-Glycerol Carbonate (S-4-[[[(4-nitrophenyl)sulfonyl]oxy]methyl]-1,3-dioxolan-2-one).

The procedure of Example 2A was again followed, except 4-nitrobenzenesulfonylchloride (2.65 g, 12 mmoles) was used instead of p-toluenesulfonylchloride to yield 2.5 g of the 4-nitrobenzenesulfonate. The product was recrystallized twice from hexane:ethyl acetate. $[\alpha]_D = +15.2$ (c=0.67, dioxane). 1HNMR (CD$_3$CN): 8.40 (d, 2H), 8.13 (d, 2H), 4.93 (m, 1H), 4.50 (t, 1H), 4.2–4.44 (m, 3H). C13NMR (CD$_3$CN): 155.42, 152.34, 141.45, 130.52, 125.81, 74.49, 70.99, 66.43.

EXAMPLE 5

R-4-[(1-naphthoxy)methyl]-1,3-dioxolan-2-one was prepared as follows:

Sodium hydride (60% suspension, 48 mg, 1.2 mmole) was placed in a round bottom flask under a nitrogen atmosphere. Dry DMF (3 ml) was added and the solution cooled to 0° C. 1-Naphthol (180 mg, 1.25 mmoles) in 2 ml DMF was added slowly over 5 minutes. The reaction was stirred for 0.5 hours. This solution was added dropwise to a cooled solution of the S-4-[[[3-nitrophenyl)sulfonyl]oxy]methyl-1,3-dioxolan-2-one (250 mg, 0.86 mmoles), prepared as exemplified above, in DMF (3 ml). The reaction was allowed to stir at 0° C. for 1 hour and at room temperature for 1 hour. The solution was diluted with 20 mls ethyl acetate and washed with water, 0.1 N NaOH, and again with water. The organic layer was dried over magnesium sulfate, filtered and the solvent removed under vacuum. The product was recrystallized from ethyl acetate: hexane to provide a pure sample of the desired product. $[\alpha]D = +40.8$ (c=0.5, dioxane). 1HNMR (DMSO): 8.06 (m, 1H), 7.88 (m, 1H), 7.4–7.6 (m, 4H), 6.97 (dd, 1H), 5.32 (m, 1H), 4.3–4.8 (m, 4H). C13NMR (DMF): 156.05, 154.47, 135.24, 128.29, 127.27, 126.74, 126.18, 125.89, 121.99, 121.49, 106.06, 75.86, 68.83, 67.32.

EXAMPLE 6

S-4-(iodomethyl)-1,3-dioxolan-2-one was prepared as follows:

The tosylate of R-glycerol carbonate (100 mg, 0.45 mmoles) was dissolved in acetone (1 ml) and sodium iodide (100 mg, 0.67 mmoles) added. The reaction was stirred at room temperature for 16 hours and the solvent removed under reduced pressure. The residue was taken up in ethyl acetate and the organic phase washed with water, sodium bicarbonate, and finally again with water. The solution was dried over magnesium sulfate, filtered and evaporated to dryness using rotoevaporator, to yield the desired optically active iodo derivative (65 mg). 1HNMR (MeCN): 4.75 (M, 1H), 4.55 (t, 1H), 4.12 (dd, 1H), 3.48 (m, 2H).

EXAMPLE 7

Enzyme catalysts were prepared as follows:

The enzymes used were 1) lipase from *Pseudomonas* ATCC 21808 (PHES8) (lyophilized fermenter broth from COGNIS Inc.), 2) lipase from *Pseudomonas ceoacia* (Amano Ps/30), 3) porcine pancreatic lipase (Sigma Chemical), 4) lipase from *Humicola languinosa* (lipolase 100T - Novo), and 5) *Candida cvlidracea* (Aldrich Chemical).

The enzyme formulation (500 mg) was dissolved in 10 ml of phosphate buffer (0.1N) and mixed with Celite 577 (2 g) which had been washed with the phosphate buffer. The water was removed from the suspension under vacuum to produce approximately 2.5 g of the biocatalyst.

EXAMPLE 8

Racemic glycerol carbonate (200 mg, 1.69 mmoles) is dissolved in 2 ml of ethyl acetate and decane (20 mg) is added as an internal standard. The acylating agent (1.69 mmoles) is added along with the biocatalyst (20 mg, formulated ATCC 21808 lipase supported on Celite 577). The reaction is stirred for the appropriate time and the enantiomeric excess of the products (TMS derivative) determined by gas chromatography using a chiral GC column (Cyclodex-B, J&W Scientific).

| Reaction | Acyl Source | Rxn Time | Conversion | Glycerol Carbonate R:S | Ester R:S |
|---|---|---|---|---|---|
| 8.A | Acetic Anhydride | 4 hours | 69% | 96:4 | 30:70 |
| 8.B | Propionic Anhydride | 1 hour | 72% | 98:2 | 24:76 |
| 8.C | Butyric Anhydride | 2 hours | 82% | 99:1 | NA |
| 8.D | Isobutyric Anhydride | 5 hours | 72% | 98:2 | NA |
| 8.E | Succinic Anhydride | 72 hours | 60% | 97:3 | NA |
| 8.F | Vinyl acetate | 8 hours | 69% | 80:20 | NA |

EXAMPLE 9

A suspension of sodium-1-naphthoxide (0.55 moles) in DMF (1.1 ml) was added slowly to a cooled solution (0° C.) of S-4-[[[(3-nitrophenyl)sulfonyl]oxy]methyl-1,3-dioxolan-2-one (150 mg, 0.511moles) in DMF (500 ul). The reaction was stirred at room temperature for 1 hour and LiCl (250 mg) added. The solution was heated to 120° C. for 2 hours and isopropylamine added (500 ul). The reaction was heated for 1 hour at 100° C. and then allowed to cool. The reaction was acidified with 0.1 N HCl and ethyl acetate (10 ml), adjusted to pH=11 with sodium hydroxide, and extracted with ethyl acetate. The organic layer was washed with water, dried over sodium sulfate and filtered. The solvent was removed under reduced pressure to yield 75 mg of S-propranolol. The crude product was recrystallized from hexanes to provide S-propranolol which was identical to an authentic sample. $[\alpha]_D = -8.1$ (EtOH, c=1).

EXAMPLE 10

The sodium salt of 4-hydroxyphenylacetamide (1.1 equivalent) is added to a solution of S-4-[[[(3-nitrophenyl)sulfonyl]oxy]methyl]-1-3-dioxolan-2-one (1 equivalent) in DMF. The reaction is allowed to stir for several hours and LiCl (2 equivalents) and potassium bicarbonate (1 equivalent) are added. The reaction heated to 120–140 degrees C. for 2 hour and then allowed to cool. Isopropylamine (10 equivalents) is added and the reaction heated to 60–100 degrees C. for 2 hours. The reaction is worked-up similar to example 9 to give S-atenolol.

EXAMPLE 11

The procedure for example 10 is followed except that the sodium salt of m-cresol is used in place of the sodium salt of 4-hydroxyphenylacetamide. The product of the reaction is S-toliprolol.

EXAMPLE 12

The enantiomeric excess of glycerol carbonate was determined by the following analytical method: Samples were derivatized by adding bis-(trimethylsilyl)-trifluoroacetamide containing 1% chlorotrimethylsilane (BSTFA reagent, Pierce) to a solution of the glycerol carbonate in an appropriate solvent (i.e. ethyl acetate). After one hour the excess BSTFA was quenched by adding t-butanol. A final concentration of ca. 0.5 mg/ml of each analyte is desired. The samples were mixed thoroughly and dispensed into autosampler vials. The samples were analyzed using the following equipment and conditions. GC:5890 Series Gas Chromatograph; GC Column: Fused Silica, 0.25 mm I.D., 5.5 meters in length; Stationary phase:Cyclodex-B (J&W Scientific), 0.25 micron film; Carrier (helium): 6.5 psi head pressure, 1.8 ml/min at 103° C.; Oven program: 103° C. (36 min isothermal hold) then 15° C./min to 210° C.; Injection port: 230° C. - split injection (100 ml/min to vent); Injection size: 1 microliter; Detector (FID) 240° C.

The various aspects of the present invention have been described and exemplified above in terms of certain preferred embodiments, various other embodiments may be apparent to those skilled in the art. The invention is, therefore, not limited to the embodiments specifically described and exemplified herein, but is capable of variation and modification without departing from the scope of the appended claims.

What is claimed is:

1. A compound of enzymatically enriched R-glycerol carbonate, having the formula

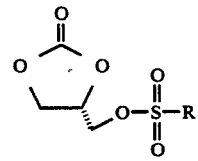

wherein R represents substituted or unsubstituted alkyl having from 1–20 carbon atoms, substituted or unsubstituted cycloalkyl having from 3 to 6 carbon atoms, said alkyl or cycloalkyl substituents being selected from the group consisting of cyclopentyl and cyclohexyl, or substituted or unsubstituted aryl having from 6–10 carbon atoms, said aryl substituents being selected from the group consisting of —$NO_2$, -halogen and alkyl.

2. S-4-[[[(4-methylphenyl)sulfonyl]oxy]methyl]-1,3-dioxolan-2-one according to claim 1.

3. S-4-[[[(4-nitrophenyl)sulfonyl]oxy]methyl]-1,3-dioxolane-2-one according to claim 1.

4. S-4-[[[(3-nitrophenyl)sulfonyl]oxy]methyl]-1,3-dioxolan-2-one according to claim 1.

5. S-4-(iodomethyl)-1,3-dioxolan-2-one according to claim 1.